United States Patent [19]

Hoshi et al.

[11] Patent Number: 4,699,979
[45] Date of Patent: Oct. 13, 1987

[54] 7-AMINO-3-PROPENYLCEPHALOSPORANIC ACID AND ESTERS THEREOF

[75] Inventors: Hideaki Hoshi, Ichikawa; Jun Okumura, Yokohama; Takayuki Naito, Kawasaki; Yoshio Abe, Shimpei Aburaki, both of Tokyo, all of Japan

[73] Assignee: Bristol-Meyers Company, New York, N.Y.

[21] Appl. No.: 843,537

[22] Filed: Mar. 25, 1986

Related U.S. Application Data

[60] Continuation-in-part of Ser. No. 725,871, Apr. 22, 1985, and Ser. No. 713,207, Mar. 18, 1985, Pat. No. 4,591,641, which is a division of Ser. No. 564,604, Dec. 28, 1983, Pat. No. 4,520,022, said Ser. No. 725,871, is a continuation-in-part of Ser. No. 564,604, , which is a continuation-in-part of Ser. No. 461,833, Jan. 28, 1983, abandoned.

[51] Int. Cl.$^4$ .................. C07D 501/22; A61K 31/545
[52] U.S. Cl. ...................................... 540/215; 540/219
[58] Field of Search ................ 540/215, 219; 514/200

[56] References Cited

U.S. PATENT DOCUMENTS

| | | | |
|---|---|---|---|
| 3,769,277 | 10/1973 | Long et al. | 260/243 C |
| 3,994,884 | 11/1976 | Weir | 260/243 C |
| 4,065,620 | 12/1977 | Webber | 544/16 |
| 4,107,431 | 8/1978 | Clark et al. | 544/16 |
| 4,110,534 | 8/1979 | Clark et al. | 544/16 |
| 4,409,214 | 10/1983 | Takaya et al. | 424/246 |
| 4,520,022 | 5/1985 | Hoshi et al. | 514/200 |

FOREIGN PATENT DOCUMENTS 1342241  1/1974  United Kingdom .

OTHER PUBLICATIONS

H. O. House et al., J. Org. Chem. 29, 3327–3333 (Nov. 1964).

*Primary Examiner*—Nicholas S. Rizzo
*Attorney, Agent, or Firm*—R. E. Carnahan

[57] ABSTRACT

This invention provides novel cephalosporin intermediates, 7β-amino-3-[(Z)-1-propen-1-yl]-3-cephem-4-carboxylic acid and esters thereof having the general formula

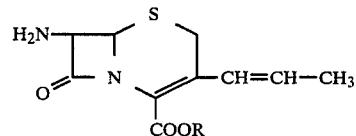

wherein the configuration of the 3-propenyl group is Z sometimes referred to as cis- and R is hydrogen or a conventional carboxy-protected group, or a physiologically hydrolyzable esterifying group, and acid addition salts thereof and the metal salts of the foregoing substance wherein R is hydrogen. These compounds are useful as intermediates for preparation of orally active cephalosporins.

12 Claims, No Drawings

7-AMINO-3-PROPENYLCEPHALOSPORANIC ACID AND ESTERS THEREOF

REFERENCE TO RELATED APPLICATIONS

This application is a continuation-in-part of application Ser. Nos. 725,871 and 713,207. The latter is a division of application Ser. No. 546,604 and the former is a continuation-in-part of application Ser. No. 564,604 which is a continuation-in-part of application Ser. No. 461,833. The status and filing dates of these prior applications are as follows.

Ser. No. 461,833 filed Jan. 28, 1983, abandoned
Ser. No. 564,604 filed Dec. 28, 1983, patented May 28, 1985, U.S. Pat. No. 4,520,022
Ser. No. 713,207 filed Mar. 18, 1985, patented May 27, 1986, U.S. Pat. No. 4,591,641
Ser. No. 725,871 filed Apr. 22, 1985, pending

DESCRIPTION OF THE PRIOR ART

U.K. Patent Specification No. 1,342,241 published Jan. 3, 1974 (corresponding to U.S. Pat. Nos. 3,769,277, and 3,994,884, granted Oct. 30, 1973, and Nov. 30, 1976) discloses the Compound VI but there is no description of 7β-amino-3-[(Z)-1-propen-1-yl]-3-cephem-4-carboxylic acid as an intermediate in the preparation thereof.

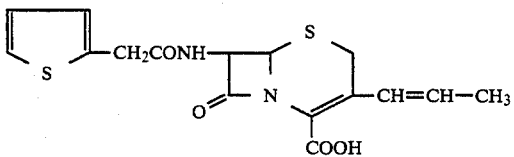

U.S. Pat. No. 4,409,214 patented Oct. 11, 1983 disclosed the preparation of Compound VII via the Wittig reaction on diphenylmethyl 7-benzylideneamino-3-triphenylphosphoniomethylceph-3-em-4-carboxylate in Preparation 38 and 39, and its use in preparing 7-acylamino derivatives of Compound VII is also disclosed at col. 42 of U.S. Pat. No. 4,107,431 patented Aug. 15, 1978, but there is no description of 7β-amino-3-[(Z)-1-propen-1-yl]-3-cephem-4-carboxylic acid, nor of any other 3-(1-propen-1-yl)-cephalosporin compound in either patent.

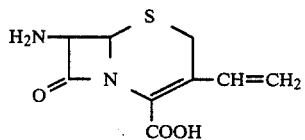

U.S. Pat. No. 4,065,620 patented Dec. 27, 1977 disclosed at col. 13 lines 39–50 several compounds similar to VII which bear a substituent such as methoxycarbonyl, carboxyl, cyano, etc. on the vinyl group.

U.S. Pat. No. 4,110,534 patented Apr. 29, 1978 is particularly concerned with preparation of compounds such as VI and VII by the Wittig reaction. Refer particularly to columns 8, 9, and 49 (Example 21).

H. O. House et al. Jour. Org. Chem. 29, 3327–3333 (1964) have studied the effect of solvents and additives including lithium salts on the proportions of cis- and trans-olefins produced in the Wittig reaction with aldehydes.

SUMMARY OF THE INVENTION

This invention relates to cephalosporin intermediates having Formula I, the synthetically useful acid addition and metal salts thereof, and to processes for their preparation.

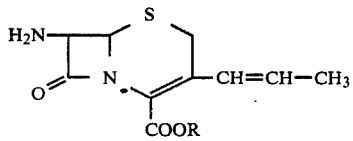

Acylation of the 7-amino group of the intermediate of Formula I yields cephalosporin antibiotics such as those referred to in U.S. Pat. No. 4,520,022 cited above, or in copending application Ser. No. 748,359 filed June 24, 1985.

In the compounds of Formula I, the configuration of the 3-propenyl group is Z- or cis-. R is hydrogen, a conventional carboxy-protecting, or a pharmaceutically acceptable esterifying group. The expression "carboxy-protecting group" refers to a protecting group of the sort conventionally used for carboxyl groups in the synthesis of cephalosporin compounds. Suitable carboxyl protecting groups include aralkyl groups such as benzyl, p-methoxybenzyl, o-nitrobenzyl, p-nitrobenzyl, and diphenylmethyl (benzhydryl), alkyl groups such as t-butyl; haloalkyl groups such as 2,2,2,-trichloroethyl, alkenyl groups such as allyl, 2-chloroallyl, alkoxymethyl groups such as methoxymethyl, 2-(trimethylsilyl)ethyl, trimethylsilyl, tert.-butyldimethylsilyl, tert.-butyldiphenylsilyl, and other carboxyl protecting groups described in the literature, for instance, in British Specification No. 1,399,086. We prefer to utilize carboxyl-protecting groups which are readily removed by treatment with acid, particularly benzhydryl or t-butyl.

Pharmaceutically acceptable esters of Formula I wherein R is a pharmaceutically acceptable esterifying group include those esters which are active per se, or which serve as pro-drugs by being hydrolyzed in the body to yield the carboxylic acid. Suitable esters of the latter type are the phenacyl, acetoxymethyl, pivaloyloxymethyl, α-acetoxyethyl, α-acetoxybenzyl, α-pivaloyloxyethyl, 3-phthalidyl, 5-indanyl, methoxymethyl, benzoyloxymethyl, α-ethylbutyryloxymethyl, propionyloxymethyl, valeryloxymethyl, isobutyryloxymethyl, glycyloxymethyl, 5-methyl-2-oxo-1,3-dioxolen-4-ylmethyl, 4-glycyloxybenzoyloxymethyl, and others known in the penicillin and cephalosporin arts.

The acid addition salts and the metal salts of the foregoing substance where R is hydrogen are also part of the present invention.

The Z-, or cis-configuration of the 3-propenyl group is a critical aspect of the present comounds. This is the characteristic which determines the advantageous Gram negative antibacterial properties of the cephalosporin end products which are the subject of the parent application Ser. No. 564,604, now U.S. Pat. No. 4,520,022.

The synthetically useful acid addition salts include the salts of Formula I with mineral acids such as hydrochloric acid, sulfuric acid and phosphoric acid, with organic sulfonic acids such as p-toluenesulfonic acid and other acids known and used in the cephalosporin arts.

Those substances of Formula I wherein R is hydrogen also form metal salts. Synthetically suitable metal salts include the sodium, potassium, calcium, magnesium, aluminum, and zinc salts.

The most preferred compounds of the invention are:
1. Diphenylmethyl 7β-amino-3-[(Z)-1-propen-1-yl]-3-cephem-4-carboxylate.
2. Diphenylmethyl 7β-amino-3-[(Z)-1-propen-1-yl]-3-cephem-4-carboxylate hydrochloride.
3. Diphenylmethyl 7β-amino-3-[(Z)-1-propen-1-yl]-3-cephem-4-carboxylate sulfate.
4. Sodium 7β-amino-3-[(Z)-1-propen-1-yl]-3-cephem-4-carboxylate.
5. Potassium 7β-amino-3-[(Z)-1-propen-1-yl]-3-cephem-4-carboxylate.
6. 7β-Amino-3-[(Z)-1-propen-1-yl]-3-cephem-4-carboxylic acid.

DETAILED DESCRIPTION OF THE INVENTION

In another aspect, this invention relates to processes for the preparation of the compounds of Formula I. Preferred procedures are shown in Reaction Schemes 1 and 2.

In Reaction Scheme 1, the diphenylmethyl group is shown as the preferred carboxy-protecting group. It will be appreciated by those skilled in the art that other carboxyl-protecting groups, well-known in the art, may be used.

In the Wittig reaction of Compound III with acetaldehyde, we have found that addition of an appropriate lithium halide such as lithium chloride, lithium bromide or lithium iodide improves the yield and proportion of Z/E isomer of the reaction product IIa. The reaction is preferably carried out with 5 to 15 chemical equivalents, preferably 10 equivalents, of lithium bromide.

Methylene chloride is the preferred reaction medium preferably containing a cosolvent such as dimethylformamide or isopropanol in minor proportions of from about 1/10 to ⅓ part by volume per part of methylene chloride. Reaction temperatures in the range of −10° C. to +25° C. are appropriate with 0° to 25° C. being preferred. The Wittig product IIa is extracted into a suitable organic solvent such as ethyl acetate and the extract is treated with Girard's reagent T to afford the 7-aminoceph-3-em compound of the present invention, Ia. Refer to Procedure 3 hereof. Subsequent treatment of Ia with trifluoroacetic acid (TFA) yields 7β-amino-3-[(Z)-1-propen-1-yl]-3-cephem-4-carboxylic acid (Ib, Procedure 7) in the ratio of Z/E=9/1. Acylation of Ib with p-hydroxyphenylglycine by a conventional acid chloride method or an activated ester method yields the orally effective cephalosporin V of the parent application Ser. No. 564,604, U.S. Pat. No. 4,520,022.

An alternative route, acylation of 7β-amino-3-propen-1-yl cephalosporin ester Ia with the N-BOC (tert.-butoxycarbonyl) blocked p-hydroxyphenylglycine in the presence of DCC (dicyclohexylcarbodiimide) and followed by deblocking with TFA (trifluoroacetic acid) also yields the cephalosporin V.

Scheme 1

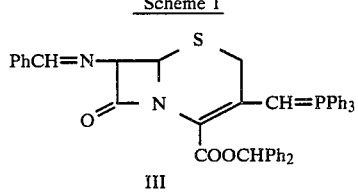

III

Procedure 3

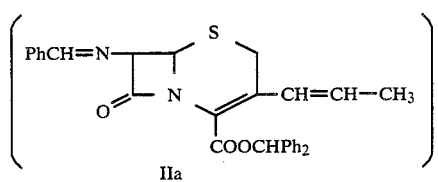

IIa

Scheme 2

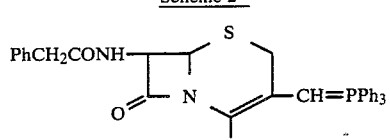

VIII

Procedure 10

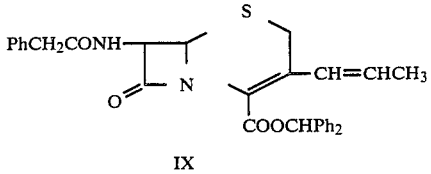

IX

Procedure 3 and 4   Procedure 11

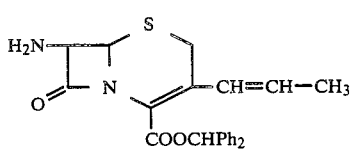

Ia

Procedure 5   Procedure 7, or 8

Scheme 1

IV: HO—C₆H₄—CH(NHBOC)—CONH—[β-lactam-cephem]—CH=CH—CH₃, COOCHPh₂

Scheme 2

Ib: H₂N—[β-lactam-cephem]—CH=CH—CH₃, COOH

Procedure 6 ↘    ↙ Procedure 9

V (BMY-28100): HO—C₆H₄—CH(NH₂)—CONH—[β-lactam-cephem]—CH=CH—CH₃, COOH

DESCRIPTION OF SPECIFIC EMBODIMENTS

The following abbreviations which appear in the experimental procedures have the meaning indicated below:

Ph=phenyl
BOC=—COOC(CH$_3$)$_3$
DCC=dicyclohexylcarbodiimide
TFA=trifluoroacetic acid
EtOAc=ethyl acetate
DMF=dimethylformamide

Procedure 1

Diphenylmethyl 7-Benzylideneamino-3-triphenylphosphoniomethyl-3-cephem-4-carboxylate Chloride To a suspension of diphenylmethyl 7-amino-3-chloromethyl-3-cephem-4-carboxylate hydrochloride (200 g, 0.44 mole) in CH$_2$Cl$_2$ (940 ml) was added 1N NaOH (440 ml) at room temperature. The mixture was shaken for 10 minutes and the organic layer was separated. To this organic layer were added MgSO$_4$ (75 g) and benzaldehyde (51 g, 0.48 mole) and the mixture was allowed to stand for 3 hours at room temperature. The reaction mixture was filtered and the insolubles were washed with CH$_2$Cl$_2$ (200 ml). To the combined filtrate and washings was added triphenylphosphine (126 g, 0.48 mole). The mixture was concentrated to about 400 ml under reduced pressure and allowed to stand for 4 days. The resulting viscous oil was diluted with ethyl acetate (1 l) and triturated to separate the title compound, a pale yellow crystalline powder which was collected by filtration and dried in vacuo. Yield 322 g (96%). M.p. 185°~190° C. (dec.).

IR: $\nu_{max}^{KBr}$ cm$^{-1}$ 1780, 1720, 1630.
UV: $\lambda_{max}^{CH2Cl2}$ nm ($\epsilon$) 260 (24100).

Procedure 2

Diphenylmethyl 7-Benzylideneamino-3-[(triphenylphosphoranylidene)-methyl]-3-cephem-4-carboxylate (III)

A mixture of diphenylmethyl 7-benzylideneamino-3-triphenylphosphoniomethyl-3-cephem-4-carboxylate chloride (322 g, 0.42 mole) and 5N Na$_2$CO$_3$ (252 ml) in CH$_2$Cl$_2$ (1.6 l) was stirred vigorously for 15 minutes at room temperature. The organic layer was separated, dried over MgSO$_4$ and concentrated to about 500 ml of volume. The concentrate was diluted with acetone (1 l), with stirring, to give a light yellow crystalline powder which was collected by filtration to yield 237 g (78%) of III, melting at 195°~198° C. (dec.).

IR: $\nu_{max}^{KBr}$ cm$^{-1}$ 1770, 1620.
UV: $\lambda_{max}^{CH2Cl2}$ nm ($\epsilon$) 254 (23000), 389 (22000).
NMR: $\delta^{CDCl3}$ ppm 2.56 & 3.16 (2H, ABq), 5.00 (1H, d, J=4 Hz), 5.23 (1H, d, J=4 Hz), 5.47 (1H, d, J=22 Hz), 6.95 (1H, s), 7.2~7.8 (30H, m), 8.55 (1H, s).

Procedure 3

Diphenylmethyl 7-Amino-3-((Z)-1-propen-1-yl)-3-cephem-4-carboxylate Hydrochloride (Ia Hydrochloride)

To a cold solution of LiBr (19 g, 216 m moles) in a mixed solvent of dry dimethylformamide (100 ml) and CH$_2$Cl$_2$ (300 ml) were added acetaldehyde (20 ml, 360 m moles) and diphenylmethyl 7-benzylideneamino-3-[(triphenylphosphoranylidene)methyl]-3-cephem-4-carboxylate (III) (15 g, 20 m moles) at −5° C. The mixture was allowed to stand for 20 hours at −5°~−10° C. and then 5 hours at room temperature. The resulting light brown solution was concentrated to ca. 100 ml of volume in vacuo and added to a two layer solvent of ethyl acetate (400 ml) and H$_2$O (400 ml). The upper layer was separated and diluted with isopropyl ether (400 ml). Silica gel (Wako gel C-100, 40 g) was added to the mixture. The mixture was shaken for 5 minutes and filtered through a pad of diatomaceous filter aid. Insolubles were washed with a mixed solvent of ethyl acetate-isopropyl ether (1/1, 200 ml). The combined filtrate and washings were concentrated to ca. 400 ml of volume. A 0.5M Girard reagent T solution in methanol (60 ml) and acetic acid (6 ml) was added to the above concentrate and the mixture was stirred for 15 minutes at room temperature. The mixture was evaporated to ca. 200 ml of volume, washed with H$_2$O (200 ml), sat. aq. NaHCO$_3$ (3×20 ml) and brine (20 ml) successively, dried over MgSO$_4$, treated with charcoal and concentrated to ca. 50 ml. To the concentrate was added N HCl in methanol (40 ml) at room temperature and left standing for 15 minutes. The mixture was evaporated to ca. 30 ml and diluted by addition of ether (300 ml). The precipitate was collected by filtration and dried over P$_2$O$_5$ to give 7.9 g of light yellow powder. A solution of the powder (7.3 g) in a mixed slvent of methanol (80 ml) and ethyl acetate (80 ml) was treated with charcoal, concentrated to ca. 100 ml, seeded with crystalline hydrochloride of the title compound, diluted slowly with ether (80 ml) and stirred for 1 hour. The separated colorless crystals were collected by filtration and dried over $P_2O_5$ in vacuo to give 6.3 g (71%) of the title compound. This product is a mixture of the isomers Z and E with reference to the propenyl moiety at the 3 position (Z/E=9/1 by HPLC) (Lichrosorb RP-18, 80% methanol-pH 7.2 phosphate buffer, 254 nm, 1 ml/min.).

IR: $\nu_{max}^{KBr}$ cm$^{-1}$ 2850, 1785, 1725.

UR: $\lambda_{max}^{EtOH}$ nm (E$_{1\ cm}$1%) 287 (173).

NMR: $\delta^{DMSO-d_6}$ ppm 1.47 (27/10H, d-d, J=7, 2 Hz, =CHCH$_3$, cis), 1.74 (3/10H, d, J=7 Hz, =CHCH$_3$, trans) 3.47 & 3.8 (each 1H, d, J=16 Hz), 5.13 (1H, d, J=4.5 Hz, 6—H), 5.23 (1H, d, J=4.5 Hz, 7—H), 5.62 (1H, d-q, J=10 & 7 Hz, 3—CH=CH), 6.24 (1H, d-d J=10 & 2 Hz, 3—CH), 6.81 (1H, s, CHPh$_2$), 7.35 (10H, m, Ph—H).

Procedure 4

Diphenylmethyl 7-Amino-3-((Z)-1-propen-1-yl)-3-cephem-4-carboxylate (Ia)

To a stirred suspension of the hydrochloride of diphenylmethyl 7-amino-3-((Z)-1-propen-1-yl)-3-cephem-4-carboxylate (5 g, 11.3 m moles) in H$_2$O (20 ml) and ethyl acetate (40 ml) was added NaHCO$_3$ until the pH of the mixture became 8. The organic layer was washed with sat. aq. NaCl (5 ml), dried over MgSO$_4$ and concentrated to ca. 20 ml of volume. The resulting solution was diluted with isopropyl ether (10 ml) and seeded with crystalline Ia. Additional isopropyl ether (30 ml) was added slowly to the mixture with stirring. After 15 minutes the separated colorless crystals were collected by filtration, washed with isopropyl ether (10 ml) and dried over P$_2$O$_5$ in vacuo to give 4.3 g (94%) of the title compound (Z/E=9/1 by HPLC) (Lichrosorb RP-18 80% methanol-pH 7.2 phosphate buffer, 254 nm, 1 ml/min.).

IR: $\nu_{max}^{KBr}$ cm$^{-1}$ 3450, 1765, 1730.

UV: $\lambda_{max}^{EtOH}$ nm (E$_{1\ cm}$1%) 289 (185).

NMR: $\delta^{CDCl_3}$ ppm 1.43 (3H, d-d, J=2 & 7 Hz, CH=CHCH$_3$), 1.66 (2H, br, s, disappeared by D$_2$O, NH$_2$), 3.23 & 3.55 (each 1H, d, J=17 Hz, 2—H), 4.73 (1H, d, J=4.5 Hz, 6—H), 4.96 (1H, d, J=4.5 Hz, 7—H), 5.46 (1H, d-q, J=10 & 7 Hz, 3—CH=CH), 6.06 (1H, br, d, J=10 Hz, 3—CH), 6.94 (1H, s, CHPh$_2$), 7.3 (10H, m, Ph—H).

Procedure 5

Diphenylmethyl 7-[(D)-α-(t-butoxycarbonylamino-α-(4-hydroxyphenyl)acetamido]-3-((Z)-1-propen-1-yl)-3-cephem-4-carboxylate (IV)

A mixture of diphenylmethyl 7-amino-3-((Z)-1-propen-1-yl)-3-cephem-4-carboxylate (Ia) (4.2 g, 10.4 m moles), (D)-α-(t-butoxycarbonylamino)-α-(4-hydroxyphenyl)acetic acid (3.3 g, 12.5 m moles) and DCC (2.6 g, 12.5 m moles) in ethyl acetate (104 ml) was stirred for 1.5 hours at room temperature. The mixture was filtered and insolubles were washed with ethyl acetate (20 ml). The filtrate and the washings were combined and washed with sat. aq. NaHCO$_3$ (3×5 ml), brine (5 ml), 10% HCl (5 ml) and brine successively, dried over MgSO$_4$, treated with charcoal and filtered. The filtrate was concentrated to ca. 10 ml and diluted with n-heptane (20 ml). The precipitate was collected by filtration and dried over P$_2$O$_5$ in vacuo. Yield 7.8 g (90% pure, quantitative in weight) as colorless powder (Z/E=9/1 based on HPLC) (Lichrosorb RP-18, 80% methanol-pH 7.2 phosphate buffer, 254 nm, 1 ml/min.).

IR: $\nu_{max}^{KBr}$ cm$^{-1}$ 3400, 1790, 1720, 1690.

UV: $\lambda_{max}^{EtOH}$ nm (E$_{1\ cm}$1%) 278 (113), 289 (115), 295 (95).

NMR: $\delta^{CDCl_3}$ ppm 1.3-1.45 (12H, m, BOC—H & =CH—CH$_3$), 3.08 & 3.33 (each 1H, d, J=18 Hz, 2—H), 4.92 (1H, d, J=4.5 Hz, 6—H), 5.06 (1H, d, J=6 Hz. s by D$_2$O, CHN), 5.5 (1H, d-q, J=10 & 7 Hz, 3—CH=CH), 5.68 (1H, d-d, J=4.5 & 8 Hz. d, J=4.5 Hz by D$_2$O, 7—H), 6.01 (1H, d, J=10 Hz, 3—CH), 6.65 & 7.08

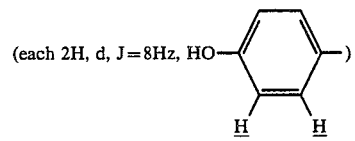

(each 2H, d, J=8Hz, HO—⟨⟩—)

6.71 (1H, d, J=8 Hz, disappeared by D$_2$O, 7—NH), 6.88 (1H, s, CHPh$_2$), 7.3 (10H, m, Ph—H).

Procedure 6

BMY-28100; 7-[(D)-2-Amino-2-(4-hydroxyphenyl)acetamido]-3-(propen-1-yl)-3-cephem-4-carboxylic Acid (V)

A mixture of diphenylmethyl 7-[(D)-α-(t-butoxycarbonylamino)-α-(4-hydroxyphenyl)acetamido]-3-((Z)-1-propen-1-yl-3-cephem-4-carboxylate (IV) which was prepared in Procedure 5 (90% pure, 7.7 g, 10.6 m moles), anisole (7.7 ml) and trifluoroacetic acid (77 ml) was stirred for 1 hour at room temperature. The mixture was concentrated in vacuo. Toluene (50 ml) was added to the concentrate and the mixture was evaporated in vacuo. Ether (200 ml) was added to the residual oil. The separated solid was collected by filtration, washed with ether (20 ml) and dried over KOH in vacuo to afford 5.3 g of trifluoroacetic acid (TFA) salt of BMY-28100. The salt (5.3 g) was dissolved in H$_2$O (100 ml), treated with charcoal and placed on a column packed with Diaion HP-20 (0.6 l). The column was washed with H$_2$O (4 l) and eluted with 40% aqueous MeOH. The methanolic fractions (1.7 l) containing the desired product were collected and evaporated to ca. 20 ml of volume. The concentrate was diluted slowly with acetone (100 ml). The separated colorless crystalline powder was collected by filtration, washed with acetone (20 ml) and dried over P$_2$O$_5$ in vacuo to give 4 g (97%) of BMY-28100 (Z/E=9/1, Zwitterion) (Lichrosorb RP-18, 20% methanol-pH 7.2 phosphate buffer, 254 nm, 1 ml/min).

Procedure 7

7-Amino-3-[(Z)-1-propen-1-yl]ceph-3-em-4-carboxylic Acid, Ib

To a stirred solution of 260 ml anisole and 1.38 l of trifluoroacetic acid (TFA) cooled to 0° C. was added 149.7 g (0.338 mole) of diphenylmethyl 7-amino-3-[(Z)-1-propen-1-yl]-3-cephem-4-carboxylic acid hydrochloride (Procedure 3 or 11). The resulting slurry was then stirred at room temperature for 1 hour. Most excess of TFA was removed in vacuo on the rotary evaporation.

The residual supernatant solution was decanted and the residual slurry was triturated with 1.5 l of dry ether during 1 hour. The crystaline product was filtered and dried over $P_2O_5$ to give 87.24 g Ib trifluoroacetate. These 87.24 g of the trifluoroacetate were suspended and stirred into 900 ml of water (pH ca. 2.5). The mixture was cooled to $+5°$ C. and then adjusted to pH 0.6 with 12N HCl. The yellow solution was charcoal treated and the slurry was filtered on a diatomaceous filter aid pad. The resulting solution was cooled to $+5°$ C. and the pH was adjusted to 2.0 with 20% NaOH. The suspension was kept 1 hour in a refrigerator to aid crystallization. The crystals were collected, washed with 800 ml of water, 800 ml of acetone and vacuum dried at room temperature. Yield 69.4 g (85.5%). Contains 9.7% of trans isomer (determined by HPLC column RP 18 MERCK; $H_2(NH_4)PO_4$, 0.1 mole 95 ml + $CH_3$ CN 5 ml; detected at 290 nm).

Procedure 8

7-Amino-3-((Z)-1-propen-1-yl)-3-cephem-4-carboxylic Acid, Ib

A solution of the phosphoranyl compound III as produced by Procedure 2 (50.0 g, 68.7 m mole) in $CH_2Cl_2$ (500 ml) was mixed with a solution of lithium bromide (29.8 g, 343 m mole) in dry DMF (170 ml) containing a small amount of $CH_2Cl_2$ (10 ml) and then with anhydrous acetaldehyde (39 ml, 687 m mole; prepared from paraldehyde and toluenesulfonic acid by distillation, according to the procedure of N. L. Drake and G. B. Cooke, Org. Syn. Col. Vol. II, p. 407). The mixture was placed in a sealed vessel and kept at 20° C. for 2 days. The reaction mixture being evaporated, the residual liquid was diluted with EtOAc (800 ml), washed with water (3×300 ml) and a saturated NaCl solution (300 ml), and evaporated to give the blocked 3-propenyl derivative IIa as foamy solid (34 g), which was used for the next reaction without further purification.

The crude IIa obtained above was treated with 98% formic acid (35 ml) and concentrated HCl (17 ml, 206 m mole) at room temperature for 1 hour. To the reaction mixture was added water (350 ml) to separate an oily layer, which was washed out with EtOAc (3×100 ml). The pH of the aqueous layer was adjusted to about 3 with 4N NaOH (ca. 65 ml) under stirring to give crystalline solid, which was collected by filtration and washed with water (50 ml) to afford the title compound (Ib, 9.7 g, 59%). HPLC [Lichrosorb RP-18, 4×300 mm, MeOH: phosphate buffer (pH 7)=15:85] showed that this product was an 83:17 mixture of Z and E isomers about the double bond of the 3-propenyl group. M.p. 200° C. (dec.).

IR: $\nu_{max}$ (KBr) in $cm^{-1}$ 3420, 1805, 1620.

UV: $\lambda_{max}$ (pH 7 phosphate buffer) in nm ($\epsilon$) 283 (8900).

PMR: $\delta(D_2O+NaHCO_3)$ in ppm 1.69 and 1.88 (3H, each d, J=6.0 Hz, Z and E of —CH=CH-$\underline{CH_3}$), 3.38 and 3.72 (2H, Abq, J=17 Hz, H—2), 5.18 (1H, d, $J_{6,7}$=5.0 Hz, H—6), 5.51 (1H, d, H—7), ca. 5.8 (1H, m, —CH=$\underline{CH}$—$CH_3$) and 6.06 (1H, d, J=11 Hz, —$\underline{CH}$=CH—$CH_3$).

Anal. Calcd. for $C_{10}H_{12}N_2O_3S$: C, 49.99; H, 5.03; N, 11.66; S, 13.34%.

Found: C, 50.20; H, 4.49; N, 10.93; S, 12.82%.

Procedure 9

7-[(D)-2-Amino-2-(4-hydroxyphenyl)acetamido]-3-((Z)-1-propen-1-yl)-3-cephem-4-carboxylic Acid, V Dimethylaniline (1.7 ml, 13.1 m mole), trimethylsilyl chloride (2.1 ml, 16.4 m mole) and trimethylamine (TEA, 2.3 ml, 16.4 m mole) were added successively to a suspension of Ib produced by Procedure 8 (1.58 g, 6.56 m mole) in $CH_2Cl_2$ (16 ml) under ice-cooling. The mixture was stirred at room temperature for 30 minutes. To the mixture was added portionwise under stirring D-p-hydroxyphenylglycyl chloride hydrochloride (1.46 g, 6.56 m mole) and the reaction was monitored by HPLC [Lichrosorb RP-18, 4×300 mm, MeOH: phosphate buffer (pH 7)=25:75]. An additional amount of the glycyl chloride was added to the mixture 3 times at 15 minute intervals (291 mg each) to complete the acylation. After the addition of dry MeOH (2.0 ml) containing dry DMF (0.1 ml), the resulting clear solution was neutralized with TEA (3.2 ml) to pH 6 and then diluted with $CH_2Cl_2$ (30 ml) to give a precipitate, which was collected by filtration and washed with $CH_2Cl_2$ (10 ml) to give the title compound as the dimethylformamide solvate (2.39 g, yield 94%; ca. 50% pure; Z/E=47:12 by HPLC).

Procedure 10

Diphenylmethyl 7-Phenylacetamido-3-((Z)-propen-1-yl)ceph-3-em-4-carboxylate, IX

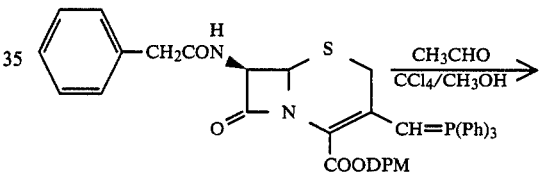
MW = 758.8

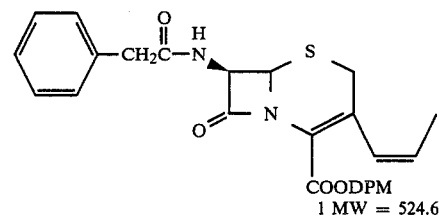
MW = 524.6

A stirred solution of 18 l of $CCl_4$, 1.8 l of methanol and 12 g of p-benzoyl benzoic acid was cooled to 8° C. and 970 ml of acetaldehyde was added. The temperature of the resulting solution rose to $+14°$ C. After five minutes, 588 g (0.7749 mole) of diphenylmethyl 7-phenylacetamido-3-[(triphenylphoranylidene)methyl]-3-cephem-4-carboxylate was added. The cooling bath was removed and the mixture vigorously stirred for 4 hours at 35° C. shaded from light under an $N_2$ atmosphere until complete dissolution of the phosphorane had occurred.

The resulting solution was vacuum concentrated and the residue was dissolved in 2 l of ethanol, and the solution was vacuum concentrated to a semi-crystallized residue which was slurried with 3 l of ethanol.

The mixture was stirred for 2 hours at $+5°$ C. and let stand overnight, crystals were collected twice, washed with ethanol, and vacuum dried at room temperature.

Yield 191 g (47%). M.p. 124°–128° C. contains 7.5% of trans isomer (determined by HPLC column Lichrosorb Si 60 5 μm Merck eluted with 85% toluene, 15% ethyl acetate).

Procedure 11

Diphenylmethyl 7-Amino-3-((Z)-propen-1-yl)ceph-3-em-4-carboxylate Hydrochloride (Ia Hydrochloride)

To a stirred solution of 159.7 g (0.767 mole) of PCl$_5$ in 2.8 l CH$_2$Cl$_2$ were added 56.7 ml (0.700 mole) of pyridine in 280 ml CH$_2$Cl$_2$ over a 20 minute period. Under a nitrogen atmosphere the slurry was cooled to 2° C. while 256 g of IX produced by Procedure 10 (0.488 mole) was added. The mixture was stirred for 40 minutes and the resulting slurry was poured rapidly into a vigorously stirred solution of 1.4 l of CH$_2$Cl$_2$, and 209 ml (2.33 moles) of 1,3-butanediol at −20° C., so that the temperature did not rise above −5° C. The cooling bath was removed and after 45 minutes the temperature rose to 10° C. and was held there for 35 minutes. Water (1.0 liter) was added and stirring continued for 5 minutes after which the layers were allowed to separate. The organic layer was washed with 600 ml of 2N HCl and then 400 ml saturated brine. The combined aqueous extracts were back-washed with 2×600 ml of CH$_2$Cl$_2$ and combined with the original CH$_2$Cl$_2$ extract.

The solution was dried over anhydrous MgSO$_4$. The MgSO$_4$ slurry was filtered and the MgSO$_4$ washed with 2×500 ml CH$_2$Cl$_2$. The combined filtrates were concentrated in vacuo on the rotary evaporator to a volume of 2.4 liters and diluted with 2.5 liters of ethyl acetate. The solution was concentrated again to a volume of ca. 1.3 liters. The resulting crystal-slurry was filtered, washed with 3×300 ml ethyl acetate. After air and vacum drying over P$_2$O$_5$ there was obtained 149.8 g of the title compound as beige crystals. Yield 69.3%.

What is claimed is:

1. A compound of the formula

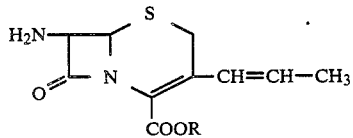

wherein the 3-propenyl group has the Z-configuration and R is hydrogen or a conventional carboxy-protecting or a pharmaceutically acceptable esterifying group, the synthetically useful acid addition salts thereof, and the synthetically useful metal salts of the foregoing substance wherein R is hydrogen.

2. A compound of the formula

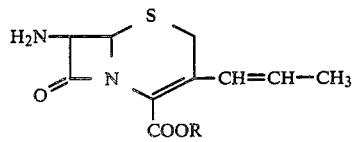

wherein the 3-propenyl group has the Z-configuration and R is hydrogen or a conventional carboxy-protecting or a pharmaceutically acceptable esterifying group, the synthetically useful acid addition salts thereof, and the synthetically useful metal salts of the foregoing substance wherein R is hydrogen, wherein said carboxy-protecting group is selected from methoxymethyl, 2,2,2-trichloroethyl, 2-(trimethylsilyl)ethyl, t-butyl, benzyl, diphenylmethyl, o-nitrobenzyl, p-nitrobenzyl, trimethylsilyl, t-butyldimethylsilyl, t-butyldiphenylsilyl, and said pharmaceutically acceptable esterifying group is selected from phenacyl, acetoxymethyl, pivaloyloxymethyl, α-acetoxyethyl, α-acetoxybenzyl, α-pivaloyloxyethyl, 3-phtalidyl, 5-indanyl, methoxymethyl, benzoyloxymethyl, α-ethylbutyryloxymethyl, propionyloxymethyl, valeryloxymethyl, isobutyryloxymethyl, glycyloxymethyl, 5-methyl-2-oxo-1, 3-dioxolen-4-ylmethyl, and 4-glycyloxybenzoyloxymethyl.

3. The compound of claim 2 wherein the acid addition salt is selected from a group consisting of hydrochloride, sulfate, p-toluenesulfate, and phosphate.

4. The compound of claim 1 wherein the metal salt is the sodium, potassium, calcium, or aluminum salt.

5. The compound of claim 2 which is diphenylmethyl 7β-amino-3-[(Z)-1-propen-1-yl]-3-cephem-4-carboxylate and the hydrochloride thereof.

6. The compound of claim 1 which is 7β-amino-3-[(Z)-1-propen-1-yl]-3-cephem-4-carboxylic acid thereof.

7. The compound of claim 1 which is 7β-amino-3-[(Z)-1-propen-1-yl]-3-cephem-4-carboxylic acid hydrochloride.

8. The compound of claim 4 which is sodium 7β-amino-3-[(Z)-1-propen-1-yl]-3-cephem-4-carboxylate.

9. The process for preparing a compound as claimed in claim 1 which comprises reacting the intermediate of the formula

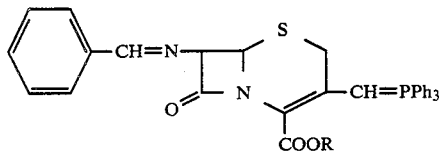

wherein R has the same meaning as in claim 1, Ph is the phenyl group with acetaldehyde in an inert organic reaction medium comprising dichloromethane, N,N'-dimethylformamide, isopropanol or a mixture thereof at a reaction temperature between 0 deg. C. and 25 deg. C. to provide a compound of the formula

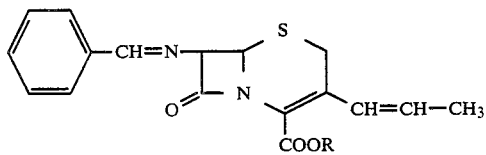

and thereafter removing the benzylidene group or both the benzylidene group and the carboxy-protecting group and, if desired, separating the 3-(Z) and 3-(E) isomers to provide the compound of the formula

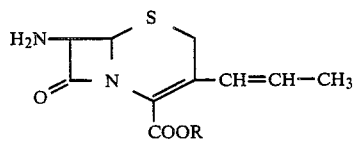

wherein R has the same meaning as in claim 1.

10. The process of claim 9 wherein the reaction with acetaldehyde is carried out in the presence of a lithium halide.

11. The process of claim 10 wherein the lithium halide is lithium chloride, lithium bromide, or lithium iodide.

12. The process of claim 10 wherein the lithium halide is lithium bromide.

* * * * *